United States Patent
Donaldson et al.

(10) Patent No.: US 11,793,820 B2
(45) Date of Patent: Oct. 24, 2023

(54) DRY POWDER FOAMABLE FORMULATIONS FOR DELIVERY OF MEDICAMENTS THROUGH THE MUCOSA

(71) Applicants: Chadwick Donaldson, San Diego, CA (US); Adam Haeberle, Franklin, TN (US); Joseph Fuisz, Nashville, TN (US)

(72) Inventors: Chadwick Donaldson, San Diego, CA (US); Adam Haeberle, Franklin, TN (US); Joseph Fuisz, Nashville, TN (US)

( * ) Notice: Subject to any disclaimer, the term of this patent is extended or adjusted under 35 U.S.C. 154(b) by 0 days.

(21) Appl. No.: 17/952,238

(22) Filed: Sep. 24, 2022

(65) Prior Publication Data
US 2023/0105232 A1 Apr. 6, 2023

Related U.S. Application Data

(60) Provisional application No. 63/247,965, filed on Sep. 24, 2021.

(51) Int. Cl.
| | |
|---|---|
| *A61K 31/66* | (2006.01) |
| *A61K 9/12* | (2006.01) |
| *A61K 9/14* | (2006.01) |
| *A61K 31/56* | (2006.01) |
| *A61K 9/00* | (2006.01) |
| *A61P 1/04* | (2006.01) |

(Continued)

(52) U.S. Cl.
CPC ........... *A61K 31/66* (2013.01); *A61K 9/006* (2013.01); *A61K 9/0031* (2013.01); *A61K 9/122* (2013.01); *A61K 9/143* (2013.01); *A61K 9/145* (2013.01); *A61K 9/146* (2013.01); *A61K 31/56* (2013.01); *A61K 31/58* (2013.01); *A61K 45/06* (2013.01); *A61P 1/04* (2018.01)

(58) Field of Classification Search
CPC ...... A61K 31/66; A61K 9/0031; A61K 9/006; A61K 9/145; A61K 9/146; A61K 31/56
See application file for complete search history.

(56) References Cited

FOREIGN PATENT DOCUMENTS

WO WO-2011053251 A1 * 5/2011 ............. A61K 31/00

OTHER PUBLICATIONS

Stokman et al, Anticancer Research 24: 3263-3268 (2004) (Year: 2004).*

* cited by examiner

*Primary Examiner* — San Ming R Hui
(74) *Attorney, Agent, or Firm* — ENTRALTA P.C.; James F. Fleming; Peter D. Weinstein

(57) ABSTRACT

Embodiments include formulations and methods for oromucosal administration of a dry powder to create a topical foam composition to deliver medicaments to an interior mucosal space, such as the oral cavity, nasal cavity, rectal cavity, vaginal cavity or esophagus. The active agent can be amifostine, an antibiotic, an anti-fungal, a non-steroidal anti-inflammatory drug or a steroidal anti-inflammatory drug. Oromucosal delivery allows one to target oral epithelial cells. Embodiments also include methods of treating mucositis. Conventional formulations and methods are generally ineffective because drugs cannot be directed toward epithelial cells of the GI that are most susceptible to mucositis. The formulations described herein increase concentration, permeability and residence time at a target site. The formulations also allow stable forms of amifostine, which obviates difficulties associated with storing, dosing and administering the drug.

18 Claims, 3 Drawing Sheets

(51) Int. Cl.
*A61K 45/06* (2006.01)
*A61K 31/58* (2006.01)

Amifostine (WR-2721)
moderately acidic (pKa1 < 2.0; pKa2 = 4.2)

Alkaline Phosphatase
(pH dependent)

Acidic environment
favors conversion

WR-1065
weak base (pKa = 9.2)

Basic environment
favors stability and
absorption

Characteristics of Various Amifostine Formulations

| Vial # | Raw Data | | | | Calculated as a Percentage | | |
| --- | --- | --- | --- | --- | --- | --- | --- |
| | Volume | Depth of Pellet | Adhesion | pH | Depth of Pellet | Adhesion | Volume |
| Control | 4.5 | 0 | 0 | - | 0.00% | 0.00% | 100.00% |
| 1 | 25.0 | 12.5 | 5.0 | 4.07 | 50.00% | 20.00% | 555.56% |
| 2 | 22.5 | 5.0 | 5.0 | 4.16 | 22.22% | 22.22% | 500.00% |
| 3 | 37.5 | 15.0 | 30.0 | 4.16 | 40.00% | 80.00% | 833.33% |
| 4 | 25.0 | 22.5 | 5.0 | 4.43 | 90.00% | 20.00% | 555.56% |
| 6 | 32.5 | 15.0 | 15.0 | 4.01 | 46.15% | 46.15% | 722.22% |
| 7 | 30.0 | 22.5 | 12.5 | 4.16 | 75.00% | 41.67% | 666.67% |
| 8 | 30.0 | 25.0 | 25.0 | 4.01 | 83.33% | 83.33% | 666.67% |
| 9 | 25.0 | 5.0 | 7.5 | 4.61 | 20.00% | 30.00% | 555.56% |
| 10 | 42.5 | 35.0 | 40.0 | 4.43 | 82.35% | 94.12% | 944.44% |
| 11 | 32.5 | 27.5 | 32.5 | 4.88 | 84.62% | 100.00% | 722.22% |
| 12 | 32.5 | 25.0 | 30.0 | 4.52 | 76.92% | 92.31% | 722.22% |
| 13 | 32.5 | 30.0 | 32.5 | 4.61 | 92.31% | 100.00% | 722.22% |

FIG. 3

DRY POWDER FOAMABLE FORMULATIONS FOR DELIVERY OF MEDICAMENTS THROUGH THE MUCOSA

FIELD OF THE INVENTION

The invention relates to therapeutic formulations, and more specifically to the use of a dry powder to create a topical foam pharmaceutical composition to deliver small molecule medicaments.

BACKGROUND

Cancer can be defined as a group of diseases that involve abnormal cell growth with the potential to invade or spread to other parts of the body. Despite advances in technology, cancer continues to be a significant cause of death and incalculable suffering. Cancer is the second most common cause of death in the United States. Patients with cancer often have limited treatment options. Treatment can include a combination of surgery, radiation therapy, chemotherapy and targeted therapy. Despite advances in research, these treatments remained relatively unchanged in recent decades. Radiation and chemotherapy typically lead to multiple side-effects including damage to epithelial cells.

Oral mucositis is a common, debilitating complication of chemotherapy and radiation. Mucositis occurs when cancer treatments break down the rapidly dividing epithelial cells lining the gastro-intestinal tract (which goes from the mouth to the anus), leaving the mucosal tissue open to ulceration and infection. It can be defined as an acute inflammation of the oral mucosa in response to systemic oncology therapy and/or radiation to fields involving the oral cavity. The clinical presentation ranges from a general erythematous oral mucosa to erosive lesions and overt ulceration. Lesions are often very painful, may compromise nutrition and oral hygiene, and can increase the risk of local and systemic infection. Furthermore, severe oral mucositis may necessitate an undesirable dose-reduction and/or a break in cancer therapy. Therefore, mucositis is a highly significant complication of cancer therapy, with a potential impact on patient prognosis.

The pathogenesis of oral mucositis is thought to involve direct and indirect mechanisms. The direct toxic effect of cytostatic agents on rapidly dividing cells of oral epithelium can result in mucosal atrophy, erythema and ulceration. Indirect stomatotoxic effects are caused by release of inflammatory mediators, loss of protective salivary constituents and therapy-induced neutropenia. Bacteria, fungi and viruses can superimpose secondary infections on the damaged mucosa. Mucositis can be described with four consecutive phases: a) the inflammatory/vascular phase (release of free radicals and cytokines); b) the epithelial phase (reduced epithelial renewal) with atrophy and ulceration; c) the ulcerative/bacterial phase (colonization mixed flora, causing release of endotoxins) with further tissue damage by stimulation of cytokines; and d) the healing phase.

There are few options for treating mucositis. Oncologists may attempt to minimize the adverse effects of cancer therapy by dose reduction. Other regimens for mucositis prevention are mainly palliative. Local and systemic analgesics are applied for pain relief while antimicrobial agents are applied for bacterial or fungal infections or for prevention. Amifostine (S-2-(3-aminopropylamino) ethyl dihydrogen phosphorothioate) can be administered as a cytoprotective adjuvant. Sold under the trade name Ethyol, amifostine is often administered in conjunction with cancer chemotherapy and radiotherapy involving DNA-binding chemotherapeutic agents.

Amifostine was originally developed as a radiation protector. Amifostine and its derivatives exert their protective effects without significantly affecting the beneficial properties of the administered therapeutic agents. This is in part due to the selective uptake of the protective thiol into normal tissue. Amifostine is commercially available as a lyophilized powder of amifostine trihydrate for reconstitution and subsequent delivery via IV infusion. Although it is FDA approved, Amifostine has limitations and many patients do not experience a benefit from using the drug. In a recent study, patients with epirubicin-induced oral mucositis were administered amifostine as an oral rinse. There was no significant difference between these patients and those who received a control (see, e.g., Stokman et al., Anticancer Res. 2004 September-October; 24(5B):3263-7).

Several factors limit the effectiveness of amifostine. Amifostine is a soluble and highly polar molecule and it is ionized in the physiological pH range. However, it is hydrolyzed in gastric pH. This leads to poor intestinal permeability and low oral absorption. Accordingly, amifostine is conventionally administered intravenously before chemotherapy or radiotherapy. While intravenous amifostine is a FDA approved therapy it does not have a high degree of use due to systemic toxicity.

Certain drug compounds like amifostine act locally in the oral cavity, pharyngeal cavity, nasal cavity, rectal cavity, vaginal cavity or esophagus. Providing a mechanism for delivery that imparts increased concentration, permeability and increased residence time at the target site is vital to the effectiveness of the product. Examples of drugs to be used in this way include amifostine in the oropharyngeal cavity or rectal cavity in prevention of radiation damage and oral mucositis or rectal bleeding, antibiotics for the treatment of gum disease, anti-fungals for the treatment of oral thrush/candidiasis in immune compromised and HIV patients and steroidal corticosteroids in the nasal cavity for treatment of polyps or in the esophagus for the treatment of eosinophilic esophagitis.

Following intravenous administration, amifostine is rapidly cleared from the plasma. The rapid clearance of amifostine is largely due to the fast conversion of amifostine to its active metabolite, WR-1065. An animal study showed that maximum tissue concentrations of WR-1065 occurred within five to fifteen minutes after amifostine injection. These results suggest that amifostine should be applied a short period (e.g., 15 to 30 minutes) before chemotherapy. Another limitation of amifostine may be due to low cellular concentrations because of the low uptake of WR-1065.

Accordingly, there is a need for a means of preventing and/or treating mucositis. This could be achieved by improving the formulation and administration of amifostine to locally target oral epithelial cells that are most susceptible to mucositis in order to have efficacy without toxicity.

Embodiments of the invention include novel formulations and improved methods of administering amifostine, antibiotics, antifungals and corticosteroids, as well as other small molecules.

SUMMARY OF THE INVENTION

The inventions described and claimed herein have many attributes and embodiments including, but not limited to, those set forth or described or referenced in this brief summary. The inventions described and claimed herein are not limited to, or by, the features or embodiments identified in this summary, which is included for purposes of illustration only and not restriction.

Embodiments include a solid foaming and expanding powder pharmaceutical carrier composition that has good and consistent flowability as a powder and is readily dispersible in the mouth and achieves a taste-masking effect that allows for ease of ingestion. This permits patients and healthcare workers to accurately measure doses and safely dispense the agent.

Thus, one embodiment is a moisture controlled stable form of amifostine, which obviates difficulties associated with handling the known amifostine. It is difficult to control the moisture content of amifostine trihydrate during drying operations and storage to meet pharmacopoeial limits of 19.2-21.2%.

One embodiment is a shelf-stable amifostine or other small molecule composition suitable for oromucosal, rectal or vaginal delivery.

One embodiment is a small molecule composition such as amifostine suitable for oromucosal use, as well as delivery to larynx and esophagus.

One embodiment is a non-aqueous (or substantially non-aqueous) formulation for oromucosal administration of amifostine. The formulation can include amifostine (5% to 40% w/w), a polyol (5% to 30% w/w), a base (5% to 30% w/w) and an acid (15% to 50% w/w). The formulation can also include a sweetener (e.g., sucralose). The base can be sodium bicarbonate and the acid can be succinic acid. In aspects, the formulation also includes a permeation enhancer and/or a film forming agent.

The formulation can be administered as an oral rinse for prevention, treatment or amelioration of an ailment such as oral mucositis. The formulation can expand upon exposure to a bodily fluid such as saliva. In aspects, the volume of the formulation increases as it effervesces. The formulation can retain the increased volume for greater than 30 second which can increase concentration, permeability and residence time in the oral cavity. At least a portion of the acid or the base can be coated for sustained production of foam. The formulation can become a sticky foam in the oral cavity. Similarly, it can become a sticky, stiff foam or a very sticky, very stiff, adherent foam.

The formulation can be administered incident to radiation or chemotherapy exposure. In aspects, the formulation is administered within about one hour before radiation exposure or chemotherapy.

Another embodiment is a non-aqueous (or substantially non-aqueous) formulation for administration of budesonide. The formulation can include budesonide (5% to 40% w/w), a polyol (5% to 30% w/w), a base (5% to 30% w/w) and an acid (15% to 50% w/w). The formulation can be administered rectally to treat ulcerative colitis. The formulation can expand upon exposure to a bodily fluid. In aspects, the volume of the formulation increases as it effervesces. The formulation can retain the increased volume for greater than 30 seconds which can increase concentration, permeability and residence time in the rectal cavity. At least a portion of the acid or the base can be coated for sustained production of foam. The formulation can become a sticky foam in the oral cavity. Similarly, it can become a sticky, stiff foam or a very sticky, very stiff, adherent foam.

In aspects, the formulations described herein can be used for treating other ailments such as eosinophilic esophagitis.

Another embodiment is a flowable powder formulation of a small molecule active agent such as amifostine. In aspects, the powder includes an effective amount of a dispersing agent.

While a flowable powder can be a preferred, a small molecule such as amifostine can have alternative formulations (e.g., tablets, orally disintegrating tablets, capsules, troches, gummies, suppositories and other solid dosage forms).

Another embodiment is a self-foaming composition, optionally in the form of a flowable powder, that further comprises chitosan. In aspects, a patient consumes the composition orally, as a rinse.

Another embodiment is an amifostine or other small molecule composition that is (or is substantially) non-aqueous and administered without water. Such compositions and formulations can be referred to as "self-foaming," insofar as the compositions foam without the administration of water or other fluid and relies on bodily fluids in situ.

Another embodiment is an amifostine (or other small molecule composition) in the form of a flowable powder, wherein water or other liquid is separately administered to the patient from the flowable powder. Another embodiment is an amifostine (or other small molecule composition) in the form of a powder, wherein the powder is mixed with water or other liquid immediately prior to administration to a mucosal cavity of a subject.

Another embodiment is an amifostine (or other small molecule composition) in the form of a flowable powder in a unit dose package. Another embodiment is an amifostine (or other small molecule) composition that is effervescent (i.e., fizzy) when administered into the mucosal cavity.

Another embodiment is a formulation for mucosal delivery of amifostine or other small molecule that includes the following components: amifostine or other small molecule (5% to 40% w/w), a dispersing agent (a polyol and/or surfactant) (5% to 30% w/w), a base (5% to 30% w/w), a negatively charged component (a chitosan or gelatin) (5% to 30% w/w), a dicarboxylic acid (15% to 50% w/w) and a sweetener (0.5% to 10% w/w). In one embodiment the base is sodium bicarbonate. In one embodiment the base is sodium carbonate or a mix of sodium bicarbonate and sodium carbonate. In one embodiment the dicarboxylic acid is succinic acid.

On certain non-limitative embodiments, the flowable powder dose weighs from 50 mg to 5 grams; preferably, 250 mg to 2 grams, more preferably 300 mg to 1.2 grams, most preferably 400 mg to 900 mg. Said weights may be exceeded in embodiments where the powder or other solid is mixed with a solvent prior to administration to the patient.

Another embodiment is a method of mucosally delivering a therapeutic amount of amifostine. Another embodiment is a method of mucosally delivering a therapeutic amount of amifostine as a radio-protectant. Another embodiment is a method of mucosally delivering a therapeutic amount of amifostine as a cryoprotectant. Another embodiment is a method of mucosally delivering a therapeutic amount of amifostine as an adjunct therapy to chemotherapy.

One embodiment is a method of mucosally delivering a therapeutic amount of amifostine, wherein the duration of the therapeutic amount is between fifteen minutes and four hours. Another embodiment is a method of mucosally delivering a therapeutic amount of amifostine to treat oral mucositis.

Another embodiment is a method of delivering a therapeutic amount of amifostine that provides a thin film of amifostine throughout or substantially throughout or generally throughout the mucosal cavity (oral, rectal or vaginal).

Another embodiment is a method of delivering a therapeutic amount of amifostine (or other small molecule) that provides a thin film of amifostine or other small molecule throughout or substantially throughout or generally throughout the oral cavity, pharynx, larynx and/or esophagus, nasal cavity, rectal cavity or vaginal cavity.

Another embodiment relates to an effervescent composition that foams, optionally without the administration of water or other administered liquid.

Another embodiment relates to an effervescent composition that creates a foam using only (or substantially only) saliva or other mucosally or bodily derived fluids.

Another embodiment relates to an effervescent composition that creates a foam using salivary fluids or other mucosally derived fluid with a volume in excess of 20 ml, preferably in excess of 30 ml. The volume can be measured in accordance with the method described in Example 1.

Another embodiment relates to an effervescent composition that creates a foam using salivary fluids or other mucosally derived fluid with a volume in excess of 30 mL, wherein said foam volume remains in excess of 30 mL, for at least 30 seconds in the mucosal cavity.

Another embodiment relates to an effervescent composition that creates a foam using salivary fluids or other mucosally derived fluid with a volume in excess of 30 ml, wherein said foam volume remains in excess of 30 ml, for at least 45 seconds in the mucosal cavity.

Another embodiment relates to an effervescent composition that creates a foam using salivary fluids or other mucosally derived fluid with a volume in excess of 30 mL, wherein said foam volume remains in excess of 30 ml, for at least 60 seconds in the mucosal cavity.

Another embodiment relates to an effervescent composition that creates a foam containing amifostine (or other drug) wherein the pH of said foam is between 4.5 and 6.0.

Another embodiment relates to an effervescent composition that creates a substantial volume of a stiff foam (defined below) from a powder formulation exposed to salivary fluids or other mucosally derived or other bodily fluid.

Another embodiment relates to an effervescent composition that creates a substantial volume of a stiff foam (or a very stiff foam) (defined below) from a powder formulation exposed to salivary fluids or other mucosally derived fluid, wherein said foam resists substantial volume degradation in the mucosal cavity.

Another embodiment relates to an effervescent composition that creates an adherent foam or a very adherent foam (both terms defined below), where the active-containing foam adheres to mucosal or other bodily surfaces.

Another embodiment relates to an effervescent composition, wherein a powder is delivered in the nose or nasal cavity, and utilizing nasal secretions forms a foam in the nasal cavity.

Another embodiment relates to a nasal composition for topical treatment of the nasal or intranasal cavity.

Another embodiment relates to an effervescent composition for intranasal delivery. One embodiment relates to an effervescent composition for intranasal delivery for systemic absorption.

Another embodiment relates to an effervescent composition for mucosal and gastrointestinal (GI) systemic absorption.

Another embodiment relates to an effervescent composition for vaginal delivery. One embodiment relates to an effervescent composition capable of coating the pelvic diaphragm.

Another embodiment of the invention relates to an effervescent composition for vaginal delivery capable of coating the introitus.

Another embodiment relates to an effervescent composition for vaginal delivery for absorption to the uterus via the uterine first pass effect.

Another embodiment of the invention relates to an effervescent composition for vaginal use that creates a foam upon exposure to vaginal secretions, optionally including menstrual fluids.

Another embodiment relates to a sustained release effervescent composition, where some (or all) of the acid or base is coated so as to result in the sustained production of foam from one second to fifteen minutes, preferably 30 seconds to eight minutes, more preferably two minutes to six minutes.

Another embodiment relates to an effervescent composition for dental use.

It is an object of certain embodiments of the invention to coat the roof of the mouth (hard palate) with the composition, and one or more active agents contained therein.

It is an object of certain embodiments of the invention to coat the soft palate with the composition, and one or more active agents contained therein.

It is an object of certain embodiments of the invention to coat the floor of the mouth and/or the lingual side of the gingiva with the composition, and one or more active agents contained therein.

It is an object of certain embodiments of the invention to coat the oropharynx (tonsil and base of tongue), the vallecula, and/or the post-cricoid region with the composition, and one or more active agents contained therein.

It is an object of certain embodiments of the invention to coat the pyriform sinus and or the aryepiglottic folds with the composition, and one or more active agents contained therein.

It is an object of certain embodiments of the invention to coat the subglottic region (the area below the vocal cords) with the composition, and one or more active agents contained therein.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 3 is a table that lists various compositions and conditions used in preparation of a foam along with output data quantitatively describing each condition and preparation.

DEFINITIONS

Figure 1:
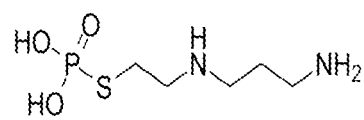
FIG. 1 is a flow chart showing the conversion of amifostine (WR-2721) to WR-1065.
Figure 1:
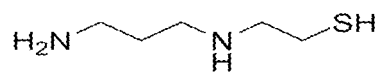

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can be in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

The term "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. An active agent can be a primary active agent, or in other words, the component(s) of a composition to which the whole or part of the effect of the composition is attributed. An active agent can be a secondary agent, or in other words, the component(s) of a composition to which an additional part and/or other effect of the composition is attributed.

A "pharmaceutical composition" can include the combination of an active agent, such as a therapeutic molecule, with a carrier, inert or active, in a sterile composition suitable for diagnostic or therapeutic use in vitro, in vivo or ex vivo.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

As used herein, the term "prevention" means all of the actions by which the occurrence of the disease is restrained, ameliorated or retarded.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

The term "administration" refers to the introduction of an amount of a predetermined substance into a patient by a certain suitable method. The composition disclosed herein may be administered via any of the common routes, as long as it is able to reach a desired tissue, for example, but is not limited to, inhaling, intraperitoneal, intravenous, intramuscular, subcutaneous, intradermal, oral, topical, intranasal, intrapulmonary, or intrarectal administration.

The term "subject" or "patient" refers to those intended to be treated with an active agent. Optionally, the subject is someone who a susceptible to mucositis or who are suspected of having or diagnosed with mucositis. However, any subject to be treated with the pharmaceutical composition disclosed herein is included without limitation. In certain embodiments, the pharmaceutical composition disclosed herein is administered to a subject to prevent and/or treat mucositis.

As applicable, the terms "about" or "generally", as used herein in the specification and appended claims, and unless otherwise indicated, means a margin of +/−20%. Also, as applicable, the term "substantially" as used herein in the specification and appended claims, unless otherwise indicated, means a margin of +/−10%. It is to be appreciated that not all uses of the above terms are quantifiable such that the referenced ranges can be applied.

The term "budesonide" refers to a corticosteroid medication. It is often administered using a metered-dose inhaler or nebulizer. It is also available as a pill, nasal spray and rectal suppository. The inhaled form is used in the long-term management of asthma and chronic obstructive pulmonary disease (COPD). The nasal spray is used for allergic rhinitis and nasal polyps. The suppository pills are formulated for delayed release and can be used for inflammatory bowel disease including Crohn's disease, ulcerative colitis, and microscopic colitis.

The term "mucosa" refers to the soft tissue that lines the body's canals and organs in the digestive, respiratory and reproductive systems. It can also be referred to as the mucous membrane. Mucosa has three layers: epithelium, lamina propria and muscularis mucosae.

The term "polyol" refers to an organic compound containing multiple hydroxyl groups. Polyols commonly used in the art include sorbitol, mannitol, xylitol, maltitol, maltitol syrup, lactitol, erythritol, and isomalt. Sugar alcohols are polyols that are derived from sugars.

The term "alkaline phosphatase" or "ALP" refers to a hydrolase intracellular enzyme that participates in the metabolic processes of cells. Amifostine can be classified as a pro-drug that is activated when dephosphorylated by ALP to its active metabolite WR-1065.

The term "GRAS" refers to "Generally Recognized As Safe." A "GRAS acid" can be, for example, glycocholic acid, hydrochloric acid, lactic acid, linoleic acid, malic acid, pectinic acid, sorbic acid, succinic acid, tannic acid, tartaric acid, taurocholic acid and thiodipropionic acid. The acid component can be used to target a mean pH in saliva of 4.5 to 6.5.

The term "oromucosal use" or "oromucosal administration" refers to the application of a drug or pharmaceutical agent through the oral mucosa, specifically the oral cavity and/or the pharynx, including one or more of the nasopharynx, oropharynx or laryngopharynx.

The term "intranasal use" or "intranasal administration" refers to the application of a drug or pharmaceutical agent to the nose, nasal cavity and/or nasopharynx.

The esophagus may also be targeted using embodiments of the present invention.

The term "intrarectal use" or "intrarectal administration" or "rectal use" or "rectal administration" refers to the application of a drug or pharmaceutical agent to the rectal cavity.

The term "vaginal use" or "vaginal administration" refers to the application of a drug or pharmaceutical agent to the vaginal cavity.

The term "stick pack" refers to a set of cylindrical shaped pouches that are each used for single serve dosage. As used herein, a single dose of an amifostine formulation (or other medicament) can be packaged in a stick pack for administration to a patient.

The term "flowable powder" refers to a powder with the capacity to move by flow that characterizes fluids and loose particulate solids. A powder substance with high flowability will have low caking and low cohesiveness. Cohesiveness is the propensity of the particles of powder to stick together and agglomerate (develop larger clusters of particles). A Powder Flow Analyser (PFA) can be used to evaluate the flow behavior of powder.

The term "dispersant" or "dispersant agent" refers to a substance, typically a surfactant, that is added to a suspension of solid or liquid particles in a liquid (such as a colloid or emulsion) to improve the separation of the particles and to prevent their settling or clumping. Flow agents may be employed to promote flow, in effective amounts. An acceptable silicate is a preferred (non limitative) flow agent.

The term "ion pair" refers to a natural species formed in solution by electrostatic interaction between oppositely charges states that are often sufficiently lipophilic to dissolve in a non-aqueous solvent.

The term "ion pairing" refers to an approach to improve the lipophilicity and subsequently the transport rate of a drug (i.e., amifostine) across lipid membranes. Lyophilization (esterification of a lipophilic moiety) of ionic drugs with high aqueous solubilities by ion-pair formation with appropriate counter-ion have proven to be successful in this regard. An ion-pair is a pair of oppositely charged ions held together by Coulombic attraction without formation of a covalent bond. They can behave like a single unit and partition into the membrane as a more lipophilic unit. This strategy involves co-administering an excess concentration of a counter-ion. Counter-ions used with amifostine for ion pairing include succinic acid, phthalic acid and benzoic acid.

The therapeutic agents in the pharmaceutical compositions can be formulated in a "therapeutically effective amount" or a "prophylactically effective amount." A "therapeutically effective amount" refers to an amount effective, at dosages and for periods of time necessary, to achieve the desired therapeutic result. A therapeutically effective amount of the recombinant vector may vary depending on the condition to be treated, the severity and course of the condition, the mode of administration, whether the peptide or agent is administered for preventive or therapeutic purposes, the bioavailability of the particular agent(s), the ability of the agent to elicit a desired response in the individual, previous therapy, the age, weight and sex of the patient, the patient's clinical history and response to the agent, the type of the therapeutic agent used, discretion of the attending physician, etc. A therapeutically effective amount is also one in which any toxic or detrimental effects of the recombinant vector are outweighed by the therapeutically beneficial effects. A "prophylactically effective amount" refers to an amount effective, at dosages and for periods of time necessary, to achieve the desired prophylactic result.

Many known and useful compounds and the like can be found in Remington's Pharmaceutical Sciences ($13^{th}$ Ed), Mack Publishing Company, Easton, Pa.—a standard reference for various types of administration. As used herein, the term "formulation(s)" means a combination of at least one active ingredient with one or more other ingredient, also commonly referred to as excipients, which may be independently active or inactive. The term "formulation" may or may not refer to a pharmaceutically acceptable composition for administration to humans or animals and may include compositions that are useful intermediates for storage or research purposes.

Other technical terms used herein convey their ordinary meaning in the art for which they are used, as exemplified by a variety of technical dictionaries. The particular values and configurations discussed in these non-limiting examples can be varied and are cited merely to illustrate at least one embodiment and are not intended to limit the scope thereof.

DETAILED DESCRIPTION

It is to be understood that both the foregoing general description and the following detailed description are exemplary and explanatory and are intended to provide further explanation of the subject technology as claimed. Additional features and advantages of the subject technology are set forth in the description below, and in part will be apparent from the description, or may be learned by practice of the subject technology. The advantages of the subject technology will be realized and attained by the structure particularly pointed out in the written description and claims hereof.

Amifostine is a pro-drug, which is active as a protective agent when dephosphorylated by alkaline phosphatase to its active metabolite WR-1065, as shown in FIG. 1. WR-1065 is preferentially taken up into normal rather than neoplastic cells because of the higher alkaline phosphatase activity, better vascularization and higher pH of normal tissue. Once inside the cell, WR-1065 protects against chemotherapy and radiation-induced damage by scavenging free radicals, donating hydrogen ions to free radicals, depleting oxygen, and direct binding to and inactivation of cytotoxic drugs. Intravenous administration of amifostine can provide protection against a broad range of cytotoxic agents. Reduction in haematological or non-haematological toxicity is described for cisplatin, carboplatin, doxorubicin, paclitaxel and 5-fluorouracil. Prevention of mucositis is mainly described in head and neck cancer patients treated with radiotherapy.

Amifostine is soluble in water and a moderately acidic compound. The conversion of amifostine to WR-1065 by alkaline phosphatase and is pH dependent, occurring more rapidly in alkaline pH. Alkaline phosphatase is a hydrolase intracellular enzyme participating in the metabolic processes of cells. Increased salivary alkaline phosphatase (ALP) levels often reflect inflammation and destruction of healthy tissues. ALP is a significant enzyme in the periodontium as it is a part of the normal turnover of the periodontal ligament, root cementum and bone homeostasis. Both the healthy and the inflamed mouth have sufficient levels of ALP that it is not a notable rate limiting step in the process of WR-2721 conversion or absorption.

This split pKa between the parent and metabolite provides a conundrum where an acidic environment is necessary for conversion of WR-2721 to WR-1065. Likewise, a basic environment confers stability to WR-2721. An environment that is too acidic decreases the amount of WR-1065 that is absorbed. An overly acidic environment can also increase acid catalyzed hydrolysis of the ester bond prior to absorption. The resulting WR-1065 is presumably further metabolized into inactive compounds resulting in a loss of radioprotective activity.

For example, amifostine is unstable at the gastric pH (i.e., pH from 1 to 3). Amifostine is hydrolyzed to WR-1065 under these acidic conditions. The hydrolysis reaction of amifostine, which appears to be pH and temperature dependent but nonenzymatic, proceeds by cleavage of the P—S bond to yield a thiol (WR-1065) and inorganic phosphate (i.e., $H_2N(CH_2)_3NH(CH_2)_2SPO_3H_2+H_2O \rightarrow H_2N(CH_2)_3NH(CH_2)_2SH+H_3PO_4$). The maximal rate of hydrolysis occurs at pH 3.0.

However, amifostine remains stable at neutral pH. In recent studies, no detectable hydrolysis occurred over four hours at room temperature at neutral pH. Because of this, the drug is stable in saliva which has a pH normal range of 6.2-7.6 (with 6.7 being the average). Resting pH of mouth does not fall below 6.3. In the oral cavity, the pH is maintained near neutrality (6.7-7.3) by saliva.

Applicants have developed a dynamic buffer system as a solution to the conundrum. The ongoing salivary production in the oral cavity (or other body cavity) during the administration and intended absorptive period of the drug is considered. Buffering agents that can be used to control pH include, for example, sodium bicarbonate, potassium bicarbonate, sodium carbonate, potassium carbonate, calcium carbonate, dipotassium phosphate, potassium citrate and sodium phosphate. The buffer system can be designed to dynamically control the pH of the product taking into consideration the effect of saliva during use (i.e., a dynamic buffer system). Examples of buffer systems to obtain the preferred pH include dibasic sodium phosphate and monobasic sodium phosphate. Both are FDA accepted buffer materials used and listed in the inactive ingredients list. For example, nicotine absorption is enhanced at Ph 7 to 8. For a pH of 7, the ratio of monobasic/dibasic can be 4.6/8.6; for a pH of 7.5 the ratio of monobasic/dibasic can be 1.9/11.9; and for a pH of 8.0 the ratio of monobasic/dibasic can be 0.6/13.4. These are mathematically calculated buffer numbers that can be adjusted according to the other ingredients added to the formulation. They can also be adjusted for the length of time designed for the dissolution of the dosage form in the target cavity.

To achieve the proper pH for both conversion and absorption, one or more acids can be added to the dry powder formulation. Acids included in the FDA SCOGS (Select Committee on GRAS Substances) database include glycocholic acid, hydrochloric acid, lactic acid, linoleic acid, malic acid, pectinic acid, sorbic acid, succinic acid, tannic acid, tartaric acid, taurocholic acid and thiodipropionic acid. The acid component can be used to target a mean pH in saliva of 4.5 to 6.5, optionally over a period of one minute range. Preferably, the acid(s) is GRAS.

In embodiments, the formulations described herein also include permeation enhancers. Permeation enhancers are substances that enhance absorption through the mucosa, mucosal coating and epithelium (otherwise known as a "penetration enhancer" or "permeability enhancer," see, e.g., U.S. Patent Application Publication No. 2006/0257463). The mucosal absorbing enhancer may include but is not limited to polyethylene glycol (PEG), diethylene glycol monoethyl ether (Transcutol), 23-lauryl ether, aprotinin, atone, benzalkomin chloride, cetylperidium chloride, cetylmethylammonium bromide, dextran sulfate, lauric acid, lauric acid/propylene glycol, lysophosphatilcholine, menthol, methoxysalicylate, oleic acid, phosphaidylcholine, polyoxyethylene, polysorbate 80, sodium EDTA, sodium glycholated, sodium glycodeoxycholate, sodium lauryl sulfate, sodium salicylate, sodium taurocholate, sodium taurodeoxycholate, sulfoxides, and various alkyl glycosides or, as described in U.S. Patent Application Publication No. 2006/0257463, bile salts, such as sodium deoxycholate, sodium glycodeoxycholate, sodium taurocholate and sodium glycocholate, surfactants such as sodium lauryl sulfate, polysorbate 80, laureth-9 benzalkonium chloride, cetylpyridinium chloride, and polyoxyethylene monoalkyl ethers such as the BRIJ® and MYRJ® series, benzoic acids, such as sodium salicylate and methoxy salicylate, fatty acids, such as lauric acid, oleic acid, undecanoic acid and methyl oleate, fatty alcohols, such as octanol and nonanol, laurocapram, the polyols, propylene glycol and glycerin, cyclodextrins, the sulfoxides, such as dimethyl sulfoxide and dodecyl methyl sulfoxide, the terpenes, such as menthol, thymol and limonene, urea, chitosan and other natural and synthetic polymers. Preferably, the mucosal absorbing enhancer is a polyol, e.g., polyethylene glycol (PEG), glycerin, maltitol, sorbitol etc. or diethylene glycol monoethyl ether (Transcutol). This list of permeation enhancers is non-limitative.

In embodiments, the formulations described herein also include "film forming agents" or "film formers" to improve adherence of the composition to an intended bodily surface. Film formers can include, for example, water soluble, water insoluble or a combination of one or more either water soluble or water insoluble polymers. The polymer may include cellulose or a cellulose derivative. Specific examples of useful water-soluble, polymers include pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch and combinations thereof. Specific examples of useful water insoluble polymers include ethyl cellulose, hydroxypropyl ethyl cellulose, cellulose acetate phthalate, hydroxypropyl methyl cellulose phthalate and combinations thereof. Other polymers useful for incorporation into the films include biodegradable polymers, copolymers, block polymers and combinations thereof. Among the known useful polymers or polymer classes which meet the above criteria are: poly (glycolic acid) (PGA), polylactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly (lactic acid)/poly(glycolic acid)/polyethyleneglycol copolymers, copolymers of polyurethane and poly(lactic acid), copolymers of polyurethane and poly(lactic acid), copolymers of alpha-amino acids, copolymers of alpha-amino acids and caproic add, copolymers of alpha-benzyl glutamate and polyethylene glycol, copolymers of succinate and poly(glycols), polyphosphazene, polyhydroxy-alkanoates and mixtures thereof. Binary and ternary systems are contemplated. Other useful and specific polymers include those marketed under the Medisorb and Biodel trademarks. The Medisorb materials are marketed by the Dupont Company and are generically identified as a "lactide/glycolide co-polymer" containing "propanoic acid, 2-hydroxy-polymer with hydroxy-polymer with hydroxyacetic acid." Four such polymers include lactide/glycolide, believed to be 100% lactide having a melting point within the range of 338-347° F. (170-175° C.); lactide/glycolide 100 L, believed to be 100% glycolide having a melting point within the range of 437-455° F. (225-235° C.); lactide/glycolide, believed to be 85% lactide and 15% glycolide with a melting point within the range of 338-347° F. (170-175° C.); and lactide/glycolide 50/50, believed to be a copolymer of 50% lactide and 50% glycolide with a melting point within the range of 338-347° F. (170-175° C.).

Amifostine Oromucosal Delivery Formulation

Mucositis often occurs when radiation or chemotherapy agents break down the epithelial cells lining the gastrointestinal (GI) tract leaving the mucosal tissue open to ulceration and infection. Amifostine is a known cyto-protectant with potential to protect certain tissues from radiation damage. It can help prevent and/or treat mucositis. However, efforts to use is clinically have been unsuccessful due to challenges related to its administration.

Only WR-2721 has a commercial potential due to the instability of WR-1065. WR-1065 was used in a clinical study to examine absorption rates through the mucosa. However, clinical studies on animals demonstrated inherent problems with this approach. Successful use of WR-2721 in animal studies requires sedation of the animal and high concentrations WR-2721 applied onto the mucosal surface for an extended time. These conditions make it impractical (if not impossible) for therapeutic use.

The same issues were encountered with clinical trials in humans. Conventional formulations of amifostine require that it remain in contact with the mucosa for an extended period of time. This is impractical because patients generally find it difficult to rinse for longer than one minute. Such rinse/contact durations do not permit sufficient absorption. Both WR-2721 and WR-1065 remain in the liquid and consequently, most remains in the rinse after it is expelled.

Further, given the location of the major salivary glands outside the accessible oral cavity the safe swallowing of a high concentration amifostine preparation allows for the amifostine product to treat these hard-to-reach areas. Given the labelled intravenous amifostine dose of 500 mg the potential toxicity or safety concern for swallowing amifostine up to 500 mg is negligible, and doses in excess of 500 mg, swallowed, may be tolerated.

Accordingly, embodiments include improved formulations for administering amifostine. The Applicant has recognized that the oral mucosa has a thin epithelium and rich vascularity, both of which favor absorption. However, contact is usually too brief for substantial absorption. A drug placed between the gums and cheek (buccal administration) or under the tongue (sublingual administration) is retained longer, enhancing absorption. Intended absorption is not limited to the oral cavity, but may also be directed to the pharynx, larynx and/or esophagus, the rectal cavity or the vaginal cavity.

A particular embodiment of the invention is an amifostine composition that has an effervescent foaming action (i.e., fizzes) in the mouth/oral cavity. This allows the delivery of a therapeutic amount of amifostine across the oral mucosa. In preferred embodiments, the amifostine is delivered as part of a non-aqueous composition without the administration of additional liquid.

In embodiments, the formulations described herein are not administered with water so as to maximize the concentration of amifostine in the oral cavity, as well as to maximize concentration of the amifostine when swallowed. Amifostine (being highly water soluble) will tend to solubilize in the saliva of the oral cavity.

Embodiments also included immediate release formulations. Thus, typically, the amifostine (or other drug or active agent) will not be coated. However, coated amifostine particles can be used to manipulate the pattern of release.

A dispersant agent, such as crospovidone, Pharmasperse 416 (available from SPI Pharma™ which contains 49.3-69.3% polyol and 30.4-50.4 calcium carbonate), isomalt maltodextrin, mannitol, maltose, sorbital, is paired with a bicarbonate foaming agent. The combination leaves a film over the oral cavity including the teeth, tongue and gums. The continued presence of WR-2721/WR-1065 as a film allows it to be absorbed for an extended period after the larger composition has been swallowed.

While the bicarbonate is necessary for the foaming nature of the product it does have the effect of increasing the pH of the environment outside the optimal range for WR-2721 conversion to WR-1065 and absorption given the much lower pKa of WR-2721. Sodium bicarbonate manifests as an odorless white crystalline powder with a slightly alkaline (bitter) taste. The pH of freshly prepared 0.1 molar aqueous solution of sodium bicarbonate is 8.3 at 77° F. and the pH of a saturated solution is 8-9.

Applicants propose an amifostine formulation for oromucosal delivery that also includes sodium bicarbonate, succinic acid, a surfactant, a polyol, a negatively charged product (chitosan or gelatin) and sucralose at a pH of about 4.5. Upon administration, the resulting solution has a consistency that allows it to cover the oral mucosal with a thin film for gradual absorption of the active agent (i.e., amifostine). In one embodiment, the amifostine solution includes the ingredients in Table 1.

TABLE 1

Amifostine Formulation

| Ingredient | Weight (mg) | Weight (%) |
|---|---|---|
| Amifostine | 150-250 | 24.6-41.0 |
| Xylitol | 50-150 | 8.2-24.6 |
| Sodium Bicarbonate | 50-150 | 8.2-24.6 |
| Succinic acid | 150-250 | 24.6-41.0 |
| Sucralose | 2-25 | 0.3-4.1 |
| Total | approx. 610 | 100 |

Succinic acid is administered (in molar excess) as a counter-ion to amifostine. Other counter-ions that can be used for ion pairing include phthalic acid and benzoic acid. The ion-pairing can improve absorption and subsequently increase local drug availability.

When placed in the mouth of a patient, amifostine will solubilize in the patient's saliva in the oral cavity.

In one aspect, the concentration of amifostine in an oromucosal delivery formulation is at least 2%, at least 5%, at least 10%, at least 15%, at least 20%, at least 25%, at least 30%, at least 35%, at least 40%, at least 50% or more. In an aspect, the concentration of amifostine in an oromucosal delivery formulation is not more than 10%, not more than 15%, not more than 20%, not more than 25%, not more than 30%, not more than 35%, not more than 40%, not more than 50% or less. In an aspect, the concentration of amifostine in an oromucosal delivery formulation is about 10%, about 15%, about 20%, about 25%, about 30%, about 35%, about 40%, about 50% or more. In an aspect, the concentration of amifostine in an oromucosal delivery formulation is from 10% to 40%, is from 15% to 35%, is from 20% to 30%, is from 25% to 30%, is from 30% to 40% or is from 40% to 50%.

In one aspect, the concentration of polyol (xylitol) in an oromucosal (or other delivery site) delivery formulation is at least 5%, at least 10%, at least 15%, at least 20%, at least 25%, at least 30%, at least 35%, at least 40% or more. In an aspect, the concentration of polyol (xylitol) in an oromucosal delivery formulation is not more than 10%, not more than 15%, not more than 20%, not more than 25%, not more than 30%, not more than 35%, not more than 40% or less. In an aspect, the concentration of polyol (xylitol) in an oromucosal delivery formulation is about 10%, about 15%, about 20%, about 25%, about 30%, about 35%, about 40% or more. In an aspect, the concentration of polyol (xylitol) in an oromucosal delivery formulation is from 5% to 10%, is from 10% to 15%, is from 15% to 25%, is from 20% to 30%, is from 25% to 30%, is from 30% to 40% or is from 40% to 50%.

In one aspect, the concentration of sodium bicarbonate in an oromucosal (or other delivery site) delivery formulation is at least 5%, at least 10%, at least 15%, at least 20%, at least 25%, at least 30%, at least 35%, at least 40% or more. In an aspect, the concentration of sodium bicarbonate in an oromucosal (or other delivery site) delivery formulation is not more than 10%, not more than 15%, not more than 20%, not more than 25%, not more than 30%, not more than 35%, not more than 40% or less. In an aspect, the concentration of sodium bicarbonate in an oromucosal (or other delivery site) delivery formulation is about 10%, about 15%, about 20%, about 25%, about 30%, about 35%, about 40% or more. In an aspect, the concentration of sodium bicarbonate in an oromucosal (or other delivery site) delivery formulation is from 5% to 10%, is from 10% to 15%, is from 15% to 25%, is from 20% to 30%, is from 25% to 30%, is from 30% to 40% or is from 40% to 50%.

In one aspect, the concentration of succinic acid in an oromucosal (or other delivery site) delivery formulation is at least 0.5%, at least 1%, at least 2%, at least 2.5%, at least 3%, at least 3.5%, at least 4%, at least 5% or more. In an aspect, the concentration of succinic acid in an oromucosal (or other delivery site) delivery formulation is not more than 1%, not more than 1.5%, not more than 2%, not more than 2.5%, not more than 3%, not more than 3.5%, not more than 4%, not more than 5% or less. In an aspect, the concentration of succinic acid in an oromucosal (or other delivery site) delivery formulation is about 1%, about 1.5%, about 2%, about 2.5%, about 3%, about 3.5%, about 4%, about 5% or more. In an aspect, the concentration of succinic acid in an oromucosal (or other delivery site) delivery formulation is from 1% to 4%, is from 1.5% to 3.5%, is from 2% to 3%, is from 2.5% to 3%, is from 3% to 4% or is from 4% to 5%.

In one aspect, one or more surfactants (such as lecithin) are included in an effervescent formulation, with a view towards achieving expanding formulations. By expanding formulation, the gas (typically carbon dioxide) emitted from the effervescence is captured in bubbles—where the "bubbles" include the now solubilized amifostine.

In this aspect, the effervescent formulation contacts with saliva, the amifostine solubilizes in saliva, and the formulation releases $CO_2$ which is captured in the amifostine-containing saliva which rapidly forms bubbles (because of the presence of the surfactant). The resulting consequence is a volumetrically expanded amifostine-containing liquid that due to its volume can rapidly coat the oral cavity.

Compositions of the present invention include drugs which are not soluble, or only partially soluble).

In aspects, when swallowed, the expanded formulation will also tend to be effective in coating the pharynx, larynx and/or esophagus.

In one aspect, the concentration of sucralose in an oromucosal delivery formulation is at least 5%, at least 10%, at least 15%, at least 20%, at least 25%, at least 30%, at least 35%, at least 40% or more. In an aspect, the concentration of sucralose in an oromucosal delivery formulation is not more than 10%, not more than 15%, not more than 20%, not more than 25%, not more than 30%, not more than 35%, not more than 40% or less. In an aspect, the concentration of sucralose in an oromucosal delivery formulation is about 10%, about 15%, about 20%, about 25%, at least 28.75%, about 30%, about 35%, about 40% or more. In an aspect, the concentration of sucralose in an oromucosal delivery formulation is from 5% to 10%, is from 10% to 15%, is from 15% to 25%, is from 20% to 30%, is from 25% to 30%, is from 30% to 40% or is from 40% to 50%.

Methods of Use

Methods for treating, preventing or ameliorating a disease, disorder, a condition, or a symptom thereof (e.g., mucositis or eosinophilic esophagitis) or a condition related thereto are provided herein using a mucosal delivery formulation for mucosal cavity delivery described herein, including without limitation to the pharynx, larynx, esophagus, nasal cavity, sinus cavity, rectal cavity and vaginal cavity.

The methods provided herein can include administering one or more of a mucosal delivery formulation described herein to mucosal cavity (i.e., to the mouth as an oral rinse) of a subject in need thereof. Preferred, but non-limiting embodiments are directed to methods for treating, preventing, inhibiting or ameliorating a disease, disorder, a condition, or a symptom related to radiation exposure or chemotherapy. For example, amifostine can be administered as an oral rinse using the formulation(s) described herein to allow absorption through the oral mucosa.

A pharmaceutical composition comprising amifostine or other small molecule drug product according to the present disclosure can be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions can include suitable solid or gel phase carriers or excipients. Exemplary carriers or excipients include calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases it will be preferable to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life or effectiveness of the therapeutic agents.

The amifostine or other small molecule drug product can be incorporated into a pharmaceutical composition suitable for mucosal administration. Suitable buffers include, for example, sodium succinate, sodium citrate, sodium phosphate or potassium phosphate. Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine. Other suitable bulking agents include glycine and arginine, which can be included at 0-0.05%. Additional surfactants include, for example, polysorbate 20 and BRIJ surfactants.

Examples of completing agents that can be used in some embodiments include β- and γ-cyclodextrin complexes, hydroxypropyl methylcellulose (e.g., Carbopol® 934), liposomes, naphthalene diamide diimide, and naphthalene diester diimide. One or more anti-oxidants can also be included, such as vitamin C, vitamin E, proanthocyanidin and α-lipoic acid typically in concentrations of 0.1%-2.5% w/w.

The amifostine or other small molecule drug product is suitably administered to the patient at one time or over a series of treatments and may be administered to the patient at any time from diagnosis onwards. The amifostine or other small molecule drug product can be administered as the sole treatment or in conjunction with other drugs or therapies useful in treating the condition in question.

Certain embodiments of the invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Administration

The composition may be self-administered or administered by a caregiver. The product may simply be placed in the oral cavity and allowed to spread, or the composition may be delivered in various locations of the mouth when administered.

In some embodiments, the patient may be instructed to assist in spreading the composition in the mucosal cavity ("patient assisted spreading"). The patient assisted spreading has a duration of 10 seconds to 120 seconds, preferably 20 seconds to 60 seconds. For an oral cavity administration, preferably during this period the patient is instructed to lead their head back to assist in coating the rear and superior reaches of the oral cavity. The patient may be instructed to shift their head from side to side. In a rectal cavity administration the patient may be instructed to lay supine and shift or roll the body from side to side over a longer duration, including time duration as long as 15 minutes or more.

For oral cavity administration, after administration and a period in the oral cavity that typically includes the "patient assisted spreading", the patient is generally instructed to swallow the composition in the mouth. Similarly, the composition may be delivered to other delivery sites, by the patient herself or by a caregiver.

For oral cavity administration, it is preferable that the swallowing occurs when the composition is still expanded and frothy. Typically, the patient is instructed to swallow within 180 seconds of administration. In aspects, the patient is instructed to swallow within 60 to 180 seconds.

A pharmaceutical composition comprising amifostine or other small molecule drug product in accordance with the present disclosure can be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions can include suitable solid or gel phase carriers or excipients. Exemplary carriers or excipients include calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases it will be preferable to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life and/or effectiveness of the therapeutic agents.

As a general proposition, a therapeutically effective amount or prophylactically effective amount of amifostine or other drug product will be administered in a range from about 1 ng/kg body weight to about 100 mg/kg body weight whether by one or more administrations. In a particular embodiment, amifostine is administered in the range of from about 1 ng/kg body weight to about 10 mg/kg body weight, about 1 ng/kg body weight to about 1 mg/kg body weight, about 1 ng/kg body weight to about 100 g/kg body weight, about 1 ng/kg body weight to about 10 g/kg body weight, about 1 ng/kg body weight/day to about 1 g/kg body weight, about 1 ng/kg body weight to about 100 ng/kg body weight, about 1 ng/kg body weight to about 10 ng/kg body weight, about 10 ng/kg body weight to about 100 mg/kg body weight, about 10 ng/kg body weight to about 10 mg/kg body weight, about 10 ng/kg body weight to about 1 mg/kg body weight, about 10 ng/kg body weight/to about 100 g/kg body weight, about 10 ng/kg body weight to about 10 mg/kg body weight, about 10 ng/kg body weight to about 1 mg/kg body weight, 10 ng/kg body weight to about 100 ng/kg body weight, about 100 ng/kg body weight to about 100 mg/kg body weight, about 100 ng/kg body weight to about 10 mg/kg body weight, about 100 ng/kg body weight to about 1 mg/kg body weight, about 100 ng/kg body weight to about 100 mg/kg body weight, about 100 ng/kg body weight to about 10 mg/kg body weight, about 100 ng/kg body weight to about 1 mg/kg body weight, about 1 mg/kg body weight to about 100 mg/kg body weight, about 1 mg/kg body weight to about 10 mg/kg body weight/day, about 1 mg/kg body weight to about 1 mg/kg body weight, about 1 mg/kg body weight to about 100 mg/kg body weight, about 1 mg/kg body weight to about 10 mg/kg body weight, about 10 mg/kg body weight to about 100 mg/kg body weight, about 10 mg/kg body weight to about 10 mg/kg body weight, about 10 mg/kg body weight to about 1 mg/kg body weight/day, about 10 mg/kg body weight to about 100 mg/kg body weight, about 100 mg/kg body weight/day to about 100 mg/kg body weight, about 100 mg/kg body weight/day to about 10 mg/kg body weight, about 100 mg/kg body weight/day to about 1 mg/kg body weight, about 1 mg/kg body weight to about 100 mg/kg body weight, about 1 mg/kg body weight to about 10 mg/kg body weight, about 10 mg/kg body weight to about 100 mg/kg body weight/day.

In other embodiments, amifostine or other drug product is administered in the range of about 10 ng to about 1 g per individual administration, about 10 ng to about 10 g per individual administration, about 10 ng to about 100 mg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 mg per individual administration, about 100 ng to about 10 mg per individual administration, about 100 ng to about 100 mg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 mg to about 10 mg per individual administration, about 1 mg to about 100 mg per individual administration, about 1 mg to about 1 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1 mg per individual administration, about 10 mg to about 10 mg per individual administration, about 10 mg to about 100 mg per individual administration, about 10 mg to about 1000 mg per injection, about 10 mg to about 10,000 mg per individual administration, about 100 mg to about 1 mg per individual administration, about 100 mg to about 10 mg per individual administration, about 100 mg to about 100 mg per individual administration, about 100 mg to about 1000 mg per injection, about 100 mg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The amifostine can be administered pursuant to chemotherapy treatments. Alternatively, it can be administered daily, BID, TID, QID, every 2, 3, 4, 5, 6 or 7 days, or every 1, 2, 3 or 4 weeks.

In other particular embodiments, the amount of the amifostine or other drug product can be administered at a dose of about 0.0006 mg, 0.001 mg, 0.003 mg, 0.006 mg, 0.01 mg, 0.03 mg, 0.06 mg, 0.1 mg, 0.3 mg, 0.6 mg, 1 mg, 3 mg, 6 mg, 10 mg, 30 mg, 60 mg, 100 mg, 300 mg, 600 mg, 1000 mg, 2000 mg, 5000 mg or 10,000 mg. As expected, the dosage will be dependent on the condition, size and age of the patient.

In other aspects, a pharmaceutical composition compound disclosed herein reduces the incidence of mucositis (e.g., signs and symptoms) by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a pharmaceutical composition disclosed herein reduces the incidence of viral infection from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition disclosed herein is in an amount sufficient to allow customary administration to an individual. In aspects of this embodiment, a pharmaceutical composition disclosed herein can be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a pharmaceutical composition. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a pharmaceutical composition. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein can comprise a solvent, emulsion or other diluent in an amount sufficient to dissolve a pharmaceutical composition disclosed herein. In other aspects of this embodiment, a pharmaceutical composition disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v).

In other aspects of this embodiment, a pharmaceutical composition disclosed herein may include a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a pharmaceutical composition disclosed herein can be of any concentration desired. In an aspect of this embodiment, the final concentration of a pharmaceutical composition in a pharmaceutical composition may be a therapeutically effective amount. In other aspects of this embodiment, the final concentration of a pharmaceutical composition in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL or at least 500 mg/mL. In other aspects of this embodiment, the final concentration of a pharmaceutical composition in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

Aspects of the present specification disclose, in part, treating an individual who is susceptible to mucositis or suffering from mucositis. As used herein, the term "treating" refers to reducing or eliminating the incidence of mucositis; or reducing the signs and symptoms. For example, the term "treating" can mean reducing a symptom of a condition characterized by a mucositis, including, but not limited to, decreasing inflammation, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. Those of skill in the art will know the appropriate symptoms or indicators associated with a specific type of ailment and will know how to determine if an individual is a candidate for treatment as disclosed herein.

In aspects of this embodiment, a therapeutically effective amount of a pharmaceutical composition disclosed herein reduces signs/symptoms of mucositis (e.g., inflammation) by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a pharmaceutical composition disclosed herein reduces signs/symptoms of mucositis by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%.

In yet other aspects of this embodiment, a therapeutically effective amount of a pharmaceutical composition disclosed herein reduces signs/symptoms of mucositis by about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a pharmaceutical composition disclosed herein generally is in the range of about 0.001 mg/kg to about 100 mg/kg and administered, for example, every 3, 5, 7, 10 or 14 days. In aspects of this embodiment, an effective amount of a pharmaceutical composition disclosed herein may be, e.g., at least 0.001 mg/kg, at least 0.01 mg/kg, at least 0.1 mg/kg, at least 1.0 mg/kg, at least 5.0 mg/kg, at least 10 mg/kg, at least 15 mg/kg, at least 20 mg/kg, at least 25 mg/kg, at least 30 mg/kg, at least 35 mg/kg, at least 40 mg/kg, at least 45 mg/kg, or at least 50 mg/kg and administered, for example, every 3, 5, 7, 10 or 14 days.

In other aspects of this embodiment, an effective amount of a pharmaceutical composition disclosed herein may be in the range of, e.g., about 0.001 mg/kg to about 10 mg/kg, about 0.001 mg/kg/day to about 15 mg/kg, about 0.001 mg/kg to about 20 mg/kg, about 0.001 mg/kg to about 25 mg/kg, about 0.001 mg/kg to about 30 mg/kg, about 0.001 mg/kg to about 35 mg/kg, about 0.001 mg/kg to about 40 mg/kg, about 0.001 mg/kg to about 45 mg/kg, about 0.001 mg/kg to about 50 mg/kg, about 0.001 mg/kg to about 75 mg/kg, or about 0.001 mg/kg to about 100 mg/kg and administered, for example, every 3, 5, 7, 10 or 14 days.

In yet other aspects of this embodiment, an effective amount of a pharmaceutical composition disclosed herein may be in the range of, e.g., about 0.01 mg/kg to about 10 mg/kg, about 0.01 mg/kg to about 15 mg/kg, about 0.01 mg/kg to about 20 mg/kg, about 0.01 mg/kg to about 25 mg/kg, about 0.01 mg/kg to about 30 mg/kg, about 0.01 mg/kg to about 35 mg/kg, about 0.01 mg/kg to about 40 mg/kg, about 0.01 mg/kg to about 45 mg/kg, about 0.01 mg/kg to about 50 mg/kg, about 0.01 mg/kg to about 75 mg/kg, or about 0.01 mg/kg to about 100 mg/kg and administered, for example, every 3, 5, 7, 10 or 14 days.

In still other aspects of this embodiment, an effective amount of a pharmaceutical composition disclosed herein may be in the range of, e.g., about 0.1 mg/kg to about 10 mg/kg, about 0.1 mg/kg to about 15 mg/kg, about 0.1 mg/kg to about 20 mg/kg, about 0.1 mg/kg to about 25 mg/kg, about 0.1 mg/kg to about 30 mg/kg, about 0.1 mg/kg to about 35 mg/kg, about 0.1 mg/kg to about 40 mg/kg, about 0.1 mg/kg to about 45 mg/kg, about 0.1 mg/kg to about 50 mg/kg, about 0.1 mg/kg to about 75 mg/kg, or about 0.1 mg/kg to about 100 mg/kg and administered, for example, every 3, 5, 7, 10 or 14 days.

Dosing can be single dosage or cumulative (serial dosing), and can be readily determined by one skilled in the art. For instance, treatment of mucositis can comprise a one-time administration of an effective dose of a pharmaceutical composition disclosed herein. Alternatively, treatment of mucositis may include multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms and/or the chemotherapy treatment plan. For example, an effective dose of a pharmaceutical composition disclosed herein can be administered to an individual once immediately after a single chemotherapy treatment. Alternatively, it can be administered daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In a further embodiment, the amifostine and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

Packaging

Where the formulation is a powder, a stickpack or sachet is a preferred embodiment. While flexible packaging is preferred, other embodiments will use non-flexible packaging-harder plastics, glass and other non-flexible materials.

Unit dose packaging is preferred, however multi-dose packaging is possible, particularly for institutional use.

In certain embodiments, it is desirable to package the product using a gas blanket, including without limitation nitrogen. The package may be vacuum sealed.

Barrier packaging can be preferred. The packaging may be packaged with a device.

In certain embodiments, the powder composition is in a soluble sachet, wherein the sachet dissolves when in contact with bodily fluids, thereby exposing the powder composition to bodily fluids.

Devices

Various devices may be employed to administer powder in or at the desired delivery site. Dry powder syringes, powder syringes, powder applicators, pessaries, tampons and other devices may be employed.

The device may be configured for nasal delivery. The device may be delivered or oral delivery; vaginal delivery; and rectal delivery.

The applicator may in certain embodiments be used to stir or agitate the foam, either prior to or following administration.

EXAMPLES

The following non-limiting examples are provided for illustrative purposes only in order to facilitate a more complete understanding of representative embodiments now contemplated. These examples are intended to be a mere subset of all possible contexts in which the components of the formulation may be combined. Thus, these examples should not be construed to limit any of the embodiments described in the present specification, including those pertaining to the type and amounts of components of the formulation and/or methods and uses thereof.

Example 1

Formulation for Oromucosal Administration of Amifostine

Conventional methods of administrating amifostine are generally ineffective. Much of the amifostine is not effectively converting to its active form (i.e., WR-1065). Further, the WR-1065 is poorly absorbed through the mucosa. The formulations described herein can increase concentration, permeability and residence time at a target site.

Figure 2:
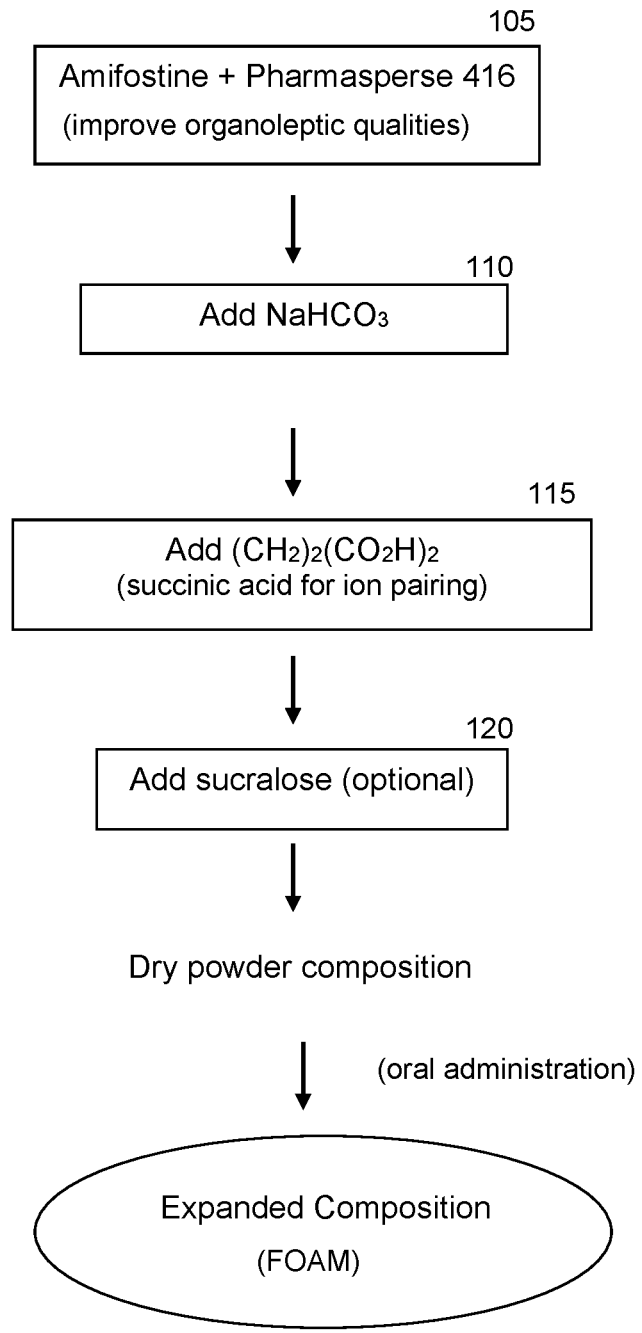
FIG. 2 is a flow chart depicting the steps in preparing an amifostine solution for oromucosal administration.

Amifostine can be prepared as a dry powder composition for oromucosal administration. Although the components can be added in any order, a process is detailed in FIG. 2. In the first step 105, amifostine is combined with Pharmasperse 416 (or other dispersing agent). Next, sodium bicarbonate is added to induce foaming 110. Succinic acid is added for ion pairing 115. Sucralose can be added 120 in an amount sufficient enough to improve taste.

In another example (summarized in Table 2), 200 mg amifostine is combined with 200 mg sodium bicarbonate, 250 mg succinic acid, 100 mg chitosan, 100 mg lecithin and 100 mg xylitol. The components are gently mixed or milled to create a homogenous formulation with even dispersion of components. The product will be a dry powder (i.e., non-aqueous) with a consistency that allows it to flow into the oral cavity and foam when exposed to saliva or other mucosal liquid. The resultant foam will cover the oral mucosal with a thin film for gradual absorption of the active agent (i.e., amifostine).

TABLE 2

Amifostine Formulation

| Ingredient | Weight (mg) | Weight (%) |
|---|---|---|
| Amifostine | 200 | 21 |
| Chitosan | 100 | 10.5 |
| Lecithin | 100 | 10.5 |
| Xylitol | 100 | 10.5 |
| Sodium Bicarbonate | 200 | 21 |
| Succinic acid | 250 | 26 |
| Total | 950 | 100 |

Upon administration, the resulting solution has a consistency that allows it to cover the oral mucosa with a thin film for gradual absorption of the active agent (i.e., amifostine). The resultant foam expands to a volume of 32.5 mL and has a pH of 4.61. The foam has excellent adhesive properties and the foam is of a solid consistency that maintains its shape for greater than one minute.

An amifostine formulation can be prepared with variations as indicated in the below table (weights listed do not include the weight of amifostine). Contents of each vial were milled prior to experimental conditions to ensure uniformity of content. Control of succinic acid, xylitol and agar was chosen to provide a base level for the increased salivary production that occurs with a change in pH and addition of a sweetener. It provides a baseline volume. All weights are in milligrams (mg).

foam to maintain contact between the drug and mucosal surfaces (or other bodily surfaces), and "firm" foam that can also help to prolong contact between the drug and mucosal surfaces (or other bodily surfaces).

Experimental formulations (Vials No. 1-13) were dissolved in 15 mL water to determine pH with a calibrated digital pH meter.

Dry powder was placed in a conical 50 mL graduated tube with 10 mL BZ108 artificial saliva formulation (5 mL for control due to corresponding lower mass), followed by 10 seconds of gentle swirling motion and inversion 3 times. Following 30 seconds the contents were measured.

Following measurement of volume a green plastic 6 mm 0.12 g standard airsoft pellet was placed in the conical tube and allowed to settle in the resultant foam for 30 seconds where the depth is measured by the volume markers. This test was intended to measure the stiffness of the foam.

Following measurement of depth the 50 mL conical tube was fully inverted for five seconds with volume remaining measured to determine adherence.

Using the test described herein, "voluminous foam" refers to foam that reaches a volume of greater than 30 mL; "very voluminous foam" is foam that reaches a volume of greater than 40 ml. "Firm foam" refers to foam in which the depth of the pellet reaches a depth of 70% (or more); "very firm" foam is a foam in which the depot of the pellet reaches a depth of 80% or more. Similarly, "sticky foam" refers to foam in which 60% or more adheres to a surface; "very sticky" foam refers to a foam in which 80% or more adheres to a surface.

For additional experiments Artificial Saliva for Pharmaceutical Research (BZ108) was obtained from BioChema Zone™, Edmonton, Alberta. Artificial Saliva for Pharmaceutical Research. Artificial Saliva is formulated according to literature for pharmaceutical research such as studies of drug dissolution and drug delivery through the oral mucosa. This is a ready-to-use formulation. The pH of the solution was 6.8.

Artificial saliva formulation has a similar composition and ingredients that simulate the mineral composition, enzymes, and pH of natural saliva. Artificial Saliva is used to study and

TABLE 3

| Vial # | Bicarb | Succinic Acid | Pharmasp 416 | Gelatin | Chitosan | Lecithin (Surfact) | Xylitol (polyol) | Agar Agar | Total Weight |
|---|---|---|---|---|---|---|---|---|---|
| Control |  | 150 |  |  |  |  | 100 | 100 | 250 |
| 1 | 150 | 250 |  |  |  |  |  |  | 400 |
| 2 | 150 | 250 | 100 |  |  |  |  |  | 500 |
| 3 | 150 | 250 | 100 | 100 |  |  |  |  | 600 |
| 4 | 150 | 250 | 100 |  | 100 |  |  |  | 600 |
| 6 | 150 | 250 | 100 |  |  | 100 |  |  | 600 |
| 7 | 150 | 250 |  |  | 100 |  |  |  | 500 |
| 8 | 150 | 250 |  |  |  | 100 |  |  | 500 |
| 9 | 200 | 250 | 100 | 100 |  | 100 |  |  | 750 |
| 10 | 200 | 250 |  | 100 |  | 100 | 100 |  | 750 |
| 11 | 200 | 250 |  |  | 100 |  | 100 |  | 650 |
| 12 | 200 | 250 |  | 200 |  |  | 100 |  | 750 |
| 13 | 200 | 250 |  |  | 100 | 100 | 100 |  | 750 |

The properties of the formulations above are described in FIG. 3. Each formulation was studied to determine volume (after fizzing), depth of pellet, adhesion and pH. All experimental conditions were completed in triplicate. The data was generated as described below.

As a general observation, it is viewed as desirable to have high volume (to distribute the drug), a "sticky" or adherent treat dry mouth and other conditions. This ready-to-use formulation contains the viscosity enhancers that mimic real human saliva.

While the test conducted is oriented to an oromucosal product, its use is expressly contemplated for delivery to vaginal and related, sites, wound care and for rectal administration.

In embodiments, a dry formulation includes the components identified in Table 4 (also described as vial #11 above). The formulation had desirable qualities of volume, depth of pellet, adhesion and pH (see FIG. 3)

TABLE 4

| Ingredient | Weight (mg) |
| --- | --- |
| Active Agent | — |
| Sodium Bicarbonate | 200 |
| Succinic acid | 150 |
| Chitosan | 100 |
| Lecithin | 100 |
| Xylitol | 100 |
| Total | 950 |

In embodiments, a dry formulation includes the components identified in Table 5 (also described as vial #13 above). The formulation also had desirable qualities of volume, depth of pellet, adhesion and pH (see FIG. 3)

TABLE 5

| Ingredient | Weight (mg) |
| --- | --- |
| Active Agent | — |
| Sodium Bicarbonate | 200 |
| Succinic acid | 150 |
| Chitosan | 100 |
| Lecithin | 100 |
| Xylitol | 100 |
| Lecithin | 100 |
| Total | 950 |

In embodiments, the concentration of the active ingredient (e.g., amifostine) can be determined by literature (i.e., published recommended doses) and methods know by those skilled in the art. Other active agents include, for example, antibiotics, anti-fungals, non-steroidal anti-inflammatory drugs and steroidal anti-inflammatory drugs.

Example 2

Formulation for Rectal Administration of Budesonside

Budesonide is a corticosteroid medication that reduces inflammation. Budesonide rectal can be used to treat distal ulcerative colitis flare (extending from the part of the large intestine that is closest to the rectum). This medication is used to treat symptoms of a certain bowel disease (ulcerative colitis). It works by reducing swelling (inflammation). Budesonide rectal is generally used once in the morning and once in the evening for two weeks. Then only once per day (at bedtime) for four more weeks.

In this example, budesonide is formulated as a foaming formulation as detailed in Table 6. The foaming formulation can be administered rectally for increased concentration, permeability and residence time at the target site. Administering it as a foam allows it to work directly on affected tissue in the bowel and rectum.

TABLE 6

| Budesonide Formulation | | |
| --- | --- | --- |
| Ingredient | Weight (mg) | Weight (%) |
| Budesonide | 200 | 21 |
| Chitosan | 100 | 10.5 |

TABLE 6-continued

| Budesonide Formulation | | |
| --- | --- | --- |
| Ingredient | Weight (mg) | Weight (%) |
| Lecithin | 100 | 10.5 |
| Xylitol | 100 | 10.5 |
| Sodium Bicarbonate | 200 | 21 |
| Succinic acid | 250 | 26 |
| Total | 950 | 100 |

Example 3

Prevention/Treatment of Mucositis in Conjunction with Chemotherapy

In this example, a patient is subject to chemotherapy as part of a treatment plan for head and neck cancer. The patient presents multiple squamous cell carcinoma tumors in the throat and larynx. The patient is administered amifostine for use after each chemotherapy session (e.g., for oral rinse within 15 minutes to two hours after chemotherapy).

The amifostine is administered to the patient in the formulation described above (Table 2). Specifically, 125 mg of amifostine is provided as an oral rinse. The patient rinses for approximately one minute and thereafter, expels/discards the rinse. The rinse process can be repeated. The radioprotective action is evident as the patient presents no signs/symptoms of mucositis during the course of chemotherapy treatment.

The study demonstrated high cellular uptake of the drug by oromucosal epithelial cells. Further, no systemic side-effects are observed and WR-1065 was well-tolerated. In this study, WR-1065 is detected in washed, isolated, vital mouth mucosa cells at a concentration of about 3.7-19.9 ng/$10^5$ cells. These findings suggest that 200 mg WR-2721 (10 ml 0.09 M) or 125 mg WR-1065 (10 ml 0.09 M) can be safely administered, and the achieved cytoprotective concentration might be effective in the prevention/treatment of mucositis.

The surprising effects achieved by the formulations and methods of the present invention are in part attributable to an improved oromucosal delivery formulation that enhances delivery of amifostine through the skin. Applicant has found that by employing the formulations described in Table 1 and Table 2, level of delivery of the amifostine into the oral epithelial cells is greatly enhanced.

Example 4

Physical Observations with a Microscope

A flexible nasopharyngoscope (Olympus) attached to a Storz Telepack video system was utilized for each evaluation. Topical decongestant and local anesthetic (Oxymetolazone and 4% lidocaine spray in a 1:1 mixture) was used in the standard fashion (i.e., two sprays in each nostril). The nasopharynx was accessed via the right nasal cavity and initial evaluation of the upper airway anatomy was visualized. Once completed, the subject placed 500 grams of the carrier compound (the composition of vial 11) mixed with 10 mg of green food coloring (Wilton powdered food coloring) in order to see extent of dispersion in the oral cavity and upper airway. As with the control compound, the upper airway was accessed via the nasal cavity. The nasopharynx, oropharynx, the hypopharynx, and laryngopharynx were all assessed. Additionally, the oral cavity was also evaluated using the video-laryngoscope to ascertain the extent that the compound was dispersed as the compound transitioned from the oral anatomic region initially and then by deglutination (initial swallow) to the upper airway. The carrier compound's broad application or dispersion throughout the upper airway was assessed by video documentation using the Olympus Laryngoscope.

The control sample was administered orally followed by closure of the mouth for 40 seconds prior to deglutination. The oral cavity was evaluated showing minimal exposure on video represented by green dye uptake and was seen on the oral tongue, but none on the hard or soft palate. The nasopharyngoscope was then passed through the right nostril to evaluate the upper airway which showed sparing of the entire nasopharynx. There was minimal to no uptake in the vallecula (area between epiglottis and base of tongue), with only mild uptake along the aryepiglottic folds (the tissue that connects the epiglottis with the larynx) with limited exposure or dispersion in the pyriform sinuses (area just lateral to the vocal cords). Additionally, the posterior pharyngeal wall was not stained and the vestibule of the larynx, the subglottis, nor the true vocal cords did not appear to have any staining or exposure to the mixture.

After administration of the test compound product into oral cavity with a closed mouth for 40 seconds without deglutination, the oral cavity was initially evaluated showing the mixture moderately present on oral tongue, roof of mouth/hard palate with delayed dispersion but moderate staining of the soft palate. Moderate dispersion/dye uptake was seen along of the floor of mouth and lingual side of the gingiva. The nasopharyngoscope was then passed through the right nostril to evaluate the upper airway which showed sparing of the entire nasopharynx. The mixture with initial coordinated swallow showed moderate evidence of staining (dispersion) of the green-colored dye into the oropharynx (tonsil and base of tongue), the vallecula, and the postcricoid region. The pyriform sinus had staining with green dye as did the area along the aryepiglottic folds. The laryngeal opening did not have any green exposure or staining based on this mixture's administration. Lastly, there was no staining of dye in the subglottic region (the area below the vocal cords).

As described above, the oromucosal amifostine formulation can be administered in a single, one-time oral rinse at the time of or soon after chemotherapy or radiation exposure. Alternatively, it can be administered once a week, once a bi-week, once a month, or from one to twelve times daily, for a period of time sufficient to alleviate a condition or symptoms, for example, for a period of time of one week, from 1 to 12 weeks or more, from 1 to 6 weeks, from 2 to 12 weeks, from 2 to 8 weeks, from 2 to 6 weeks, from 2 to 4 weeks, from 4 to 12 weeks, from 4 to 8 weeks, or from 4 to 6 weeks. The present compositions can be administered, for example, at a frequency of once per day to hourly if needed. The presently described formulations can be administered once or more per day for a period of time from 1 week to 4 weeks, of from 1 week to 2 weeks, for 1 week, for 2 weeks, for 3 weeks, or for 4 weeks or more. In some instances, it may also be desirable to continue treatment indefinitely, for example, to inhibit recurring inflammation. A suitable administration for a oromucosal delivery formulation comprising an oral rinse, for example is once, twice, three, four times daily, or hourly if needed.

If desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

In embodiments, a dry powder composition described herein expands when combined with a bodily fluid (e.g., saliva). In aspects, the volume of the dry powder composition expands by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least two times, at least three times, at least four times, at least five times, at least six times, at least eight times or at least ten times its original (i.e., dry) volume.

In aspects, the expanded composition maintains its expanded volume (or at least 80% of its volume) for at least 10 seconds, at least 20 seconds, at least 30 seconds, at least 1 minute, at least 2 minutes, at least 3 minutes, at least 5 minutes, at least 7 minutes, at least 8 minutes, at least 10 minutes, at least 12 minutes or at least 15 minutes.

In aspects, the expanded composition has improved adhesion to a target site (e.g., mucosa). In aspects, the expanded composition has greater homogeneity (i.e., more uniform distribution of an active agent). In aspects, the expanded composition provides a higher rate of penetration and/or permeation into and/or through the mucosa. In aspects, the methods described herein allow for smaller doses of a medicament because of improved administration to a target tissue.

In aspects, an active agent used with the compositions describe herein. The active agent can be one or more of an anesthetics, an anti-allergic agent, a dermatic, a chemotherapy drug, quinine, an antimycotic, an antibiotic, thalidomide, serotonin, a eicosanoid, an analgesic, an anticonvulsant, a nonsteroidal antirrheumatic, a leukotriene, a leukotriene inhibitor, an androgen, an antiandrogen, a corticoid, an opiate, a receptor antagonist, a blood clotting inhibitory substance, a thrombocyte aggregation inhibitor, a histamine antagonist, a peptides/proteins, a nucleic acid, an antipruritic, an antidiabetic, a prostaglandin, a prostaglandin synthesis inhibitor, an antiviral-acting or virostatic-acting substance, an antimicrobial-acting substance, an immune suppressant, a hormone, an agent for treatment of warts or wounds, a vitamin, a plant extract or essence of plant extract, a psychoactive drug, an analeptic, a muscle relaxant, an antiepileptic, an antiparkinson agent, an antiemetic, an antiparasitic, a ganglion-active substance, a sympathetic-active substance, a parasympathetic-active substance, an antibacterial-acting drug, a calcium antagonist, a cardiovascular agent, an antiasthmatic, an antitussive, an expectorants, a hepatic, a diuretic, a choleretic, a disinfectant, a trace element, an antiinfective, a cytostatic, an antimetabolite, a hormone antagonist, an anti-fungal or an immune modulator.

It is understood that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; the area to be treated and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time can be determined by methods well known in the art.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. The pharmaceutical composition may also be formulated into solutions, suspensions, tablets, pills, capsules and long-acting preparations.

On the other hand, examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition disclosed herein are determined by the type of active ingredient, together with various factors such as the disease to be treated, administration route, patient's age, gender, and body weight, and disease severity.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the agent disclosed herein may be approximately 0.0001 μg to 500 mg per 1 kg of body weight of a patient. However, the effective dose of the agent is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects.

Moreover, the pharmaceutical composition may be administered alone or in combination or coincident with other pharmaceutical formulations showing prophylactic or therapeutic efficacy.

Given the teachings and guidance provided herein, those skilled in the art will understand that a formulation described herein can be equally applicable to many types of biopharmaceuticals, including those exemplified, as well as others known in the art. Given the teachings and guidance provided herein, those skilled in the art also will understand that the selection of, for example, type(s) or and/or amount(s) of one or more excipients, surfactants and/or optional components can be made based on the chemical and functional compatibility with the biopharmaceutical to be formulated and/or the mode of administration as well as other chemical, functional, physiological and/or medical factors well known in the art. For example, non-reducing sugars exhibit favorable excipient properties when used with polypeptide biopharmaceuticals compared to reducing sugars. Accordingly, exemplary formulations are exemplified further herein with reference to polypeptide biopharmaceuticals. However, the range of applicability, chemical and physical properties, considerations and methodology applied to polypeptide biopharmaceutical can be similarly applicable to biopharmaceuticals other than polypeptide biopharmaceuticals.

In various embodiments, a formulation can include, one or more preservatives and/or additives known in the art. Similarly, a formulation can further be formulated, without limitation, into any of various known delivery formulations. For example, in an embodiment, a formulation can include, surfactants, adjuvant, biodegradable polymers, hydrogels, etc., such optional components, their chemical and functional characteristics are known in the art. Similarly known in the art are formulations that facilitate rapid, sustained or delayed release of the bioactive agents after administration. A formulation as described can be produced to include these or other formulation components known in the art.

In certain embodiments, kits can comprise, without limitation, one or more single or multi-chambered syringes (e.g., liquid syringes and lyosyringes) for administering one or more formulations described herein. In various embodiments, the kit can comprise formulation components for parenteral, subcutaneous, intramuscular or IV administration, sealed in a vial under partial vacuum in a form ready for loading into a syringe and administration to a subject. In this regard, the composition can be disposed therein under partial vacuum. In all of these embodiments and others, the kits can contain one or more vials in accordance with any of the foregoing, wherein each vial contains a single unit dose for administration to a subject.

The kits can comprise lyophilates, disposed as herein, that upon reconstitution provide compositions in accordance therewith. In various embodiment the kits can contain a lyophilate and a sterile diluent for reconstituting the lyophilate.

Also described herein, are methods for treating a subject in need of therapy, comprising administering to the subject an effective amount of a formulation as described herein. The therapeutically effective amount or dose of a formulation will depend on the disease or condition of the subject and actual clinical setting.

In an embodiment, a formulation as described herein can be administered by any suitable route, specifically by parenteral (including subcutaneous, intramuscular, intravenous and intradermal) administration. It will also be appreciated that the preferred route will vary with the condition and age of the recipient, and the disease being treated. Methods of determining the most effective means and dosage of administration are known to those of skill in the art and will vary, without limitation, with the composition used for therapy, the purpose of the therapy, and the subject being treated. Single or multiple administrations can be carried out, without limitation, the dose level and pattern being selected by the treating physician. Suitable dosage formulations and methods of administering the agents are known in the art.

The formulations as described herein can be used in the manufacture of medicaments and for the treatment of humans and other animals by administration in accordance with conventional procedures.

Also provided herein are combinatorial methods for developing suitable virus formulations using combinations of amino acids. These methods are effective for developing stable liquid or lyophilized formulations, and particularly pharmaceutical virus formulations.

Compositions in accordance with embodiments described herein have desirable properties, such as desirable solubility, viscosity, syringeability and stability. Lyophilates in accordance with embodiments described herein have desirable properties, as well, such as desirable recovery, stability and reconstitution.

In an embodiment, the pH of the pharmaceutical formulation is at least about 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, or 9.

In an embodiment, the pH of the pharmaceutical formulation is from about 3 to about 9, about 4 to about 19, about 5 to about 9, about 6 to about 8, about 6 to about 7, about 6 to about 9, about 5 to about 6, about 5 to about 7, about 5 to about 8, about 4 to about 9, about 4 to about 8, about 4 to about 7, about 4 to about 6, about 4 to about 5, about 3 to about 8, about 3 to about 7, about 3 to about 6, about 3 to about 5, about 3 to about 4, about 7 to about 8, about 7 to about 9, about 7 to about 10.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A method of preventing or treating mucositis in a subject, the method comprising oromucosal administration of a formulation comprised of:
   a) amifostine trihydrate (5% to 40% w/w),
   b) a polyol (5% to 30% w/w),
   c) a base (10% to 40% w/w), and
   d) an acid (15% to 50% w/w),
   wherein the base induces foaming of the formulation to increase one or more of surface area and volume of the amifostine trihydrate at or near epithelial cells of the mouth and GI tract.

2. The method of claim 1, wherein the mucositis is incident to radiation exposure or chemotherapy.

3. The method of claim 1, wherein the volume of the formulation increases upon exposure to saliva.

4. The method of claim 3, wherein the formulation remains at an increased volume for at least 30 seconds.

5. The method of claim 1, wherein the formulation further comprises a sweetener.

6. The method of claim 1, wherein the base is sodium bicarbonate.

7. The method of claim 1, wherein the acid is succinic acid.

8. The method of claim 1, wherein the formulation further comprises a permeation enhancer.

9. The method of claim 1, wherein the formulation further comprises a film forming agent.

10. A method of administering a medicament to mucosal epithelial cells, the method comprised of inducing foaming of a dry formulation by contacting the dry formulation with a bodily fluid to increase one or more of surface area, volume and stickiness of the medicament at a target site, wherein the formulation is comprised of:
    a) the medicament (1% to 40% w/w),
    b) a polyol (5% to 30% w/w),
    c) a base (5% to 30% w/w), and
    d) an acid (15% to 50% w/w).

11. The method of claim 10, wherein the medicament is amifostine trihydrate, budesonide, an antibiotic, an antifungal agent or a corticosteroid.

12. The method of claim 10, wherein the target site is the oral cavity or the rectal cavity.

13. The method of claim 10, wherein the volume of the dry formulation increases upon exposure to the bodily fluid and wherein the formulation remains at an increased volume for at least 30 seconds.

14. A method of preventing or treating mucositis, the method comprising administering a formulation of amifostine trihydrate to subject by:
    a) administering the formulation as a dry powder orally to the subject,
    b) wherein the formulation comprises a base to induce foaming of the formulation upon contact with saliva,
    c) wherein the formulation comprises a polyol to increase the firmness and/or consistency of the formulation upon foaming, and
    d) wherein the formulation comprises an acid as a counter-ion to increase foaming and/or control pH.

15. The method of claim 14, wherein the base is sodium bicarbonate.

16. The method of claim 14, wherein the formulation further comprises a negatively charged excipient to improve mucosal binding.

17. The method of claim 16, wherein negatively charged excipient is selected from one or more of chitosan, chitan and gelatin.

18. The method of claim 14, wherein the volume of the formulation after foaming from contact with the saliva is 30 mL or more.

* * * * *